(12) United States Patent
Morley et al.

(10) Patent No.: US 8,585,968 B2
(45) Date of Patent: Nov. 19, 2013

(54) METHOD AND SYSTEM FOR PURGING MOISTURE FROM AN OXYGENATOR

(76) Inventors: Scott W. Morley, Pittsburgh, PA (US); Paul Bieniek, Pittsburgh, PA (US); Meir Rosenberg, Newton, MA (US)

( * ) Notice: Subject to any disclaimer, the term of this patent is extended or adjusted under 35 U.S.C. 154(b) by 1030 days.

(21) Appl. No.: 12/608,808

(22) Filed: Oct. 29, 2009

(65) Prior Publication Data

US 2010/0101657 A1 Apr. 29, 2010

Related U.S. Application Data

(63) Continuation-in-part of application No. 11/408,650, filed on Apr. 21, 2006, now Pat. No. 7,927,544.

(51) Int. Cl.
*A61M 1/00* (2006.01)

(52) U.S. Cl.
USPC .............................. 422/45; 604/6.14; 210/645

(58) Field of Classification Search
CPC ....................................................... A61M 1/36
USPC ............... 604/6.01, 6.09, 6.14; 210/645, 646; 442/45, 48
See application file for complete search history.

(56) References Cited

U.S. PATENT DOCUMENTS

| | | | |
|---|---|---|---|
| 3,841,837 A | 10/1974 | Kitrilakis et al. | |
| 4,722,725 A | 2/1988 | Sawyer et al. | |
| 4,740,313 A | 4/1988 | Schoendorfer et al. | |
| 5,236,665 A | 8/1993 | Mathewson et al. | |
| 5,263,924 A | 11/1993 | Mathewson | |

(Continued)

FOREIGN PATENT DOCUMENTS

| | | |
|---|---|---|
| DE | 103 41 221 A1 | 3/2005 |
| WO | WO 94/03266 A1 | 2/1994 |

(Continued)

OTHER PUBLICATIONS

Federspiel, W. et al, "Gas Flow Dynamics in Hollow Fiber Membranes", AIChE Journal, 42:7, 2094-2099. (1996).*

(Continued)

*Primary Examiner* — Melanie Hand
(74) *Attorney, Agent, or Firm* — Kathleen Kuznicki; Lynch Weis, LLC

(57) ABSTRACT

A method and system for improving gas exchange properties of oxygenators which utilize hollow fiber membranes for removing carbon dioxide or adding oxygen to a patient's blood via extracorporeal circulation by removing moisture accumulating in the fibers are disclosed. The system utilizes a vacuum source for drawing sweep gas into the oxygenator, a moisture collection unit for storing moisture removed from the oxygenator, the moisture collecting unit being in communication with the oxygenator and the vacuum source and a flow control mechanism having an open position which allows sweep gas exiting the oxygenator to flow to the moisture collecting unit and a closed position which stops the flow of sweep gas from the oxygenator to the moisture collecting unit. The vacuum source draws sweep gas through the oxygenator and moisture collecting unit when the flow control mechanism is in the open position and the vacuum source creates a vacuum buildup in the moisture collecting unit when the flow control mechanism is in the closed position. The vacuum in the moisture collecting unit provides a sudden increase to the flow rate of the sweep gas to draw moisture with the sweep gas exiting the oxygenator when the flow control mechanism is returned to the open position.

20 Claims, 2 Drawing Sheets

(56) References Cited

U.S. PATENT DOCUMENTS

| | | | |
|---|---|---|---|
| 5,266,265 A | 11/1993 | Raible | |
| 5,270,005 A | 12/1993 | Raible | |
| 5,411,706 A | 5/1995 | Hubbard et al. | |
| 5,591,404 A | 1/1997 | Mathewson | |
| 5,634,892 A | 6/1997 | Whalen | |
| 5,695,717 A | 12/1997 | Polaschegg et al. | |
| 5,823,987 A | 10/1998 | Elgas et al. | |
| 5,830,370 A | 11/1998 | Maloney et al. | |
| 5,900,142 A | 5/1999 | Maloney, Jr. et al. | |
| 6,099,730 A | 8/2000 | Ameer et al. | |
| 6,106,776 A | 8/2000 | Borovetz et al. | |
| 6,217,826 B1 | 4/2001 | Reeder et al. | |
| 6,348,175 B1 | 2/2002 | Borovetz et al. | |
| 6,368,557 B1 | 4/2002 | Piplani et al. | |
| 6,387,323 B1 | 5/2002 | Afzal et al. | |
| 6,428,747 B1 | 8/2002 | Dueri et al. | |
| 6,454,999 B1 | 9/2002 | Farhangnia et al. | |
| 6,863,821 B2 | 3/2005 | Moriarty et al. | |
| 2005/0118059 A1 | 6/2005 | Olsen et al. | |
| 2008/0199357 A1 | 8/2008 | Gellman et al. | |
| 2009/0220388 A1 | 9/2009 | Monzyk et al. | |

FOREIGN PATENT DOCUMENTS

| | | | | |
|---|---|---|---|---|
| WO | WO 96/16684 A1 | 6/1996 | | |
| WO | WO 00/38817 A1 | 7/2000 | | |
| WO | WO 03092776 A2 | * 11/2003 | ............ | A61M 16/00 |
| WO | WO 2006/031858 A1 | 3/2006 | | |
| WO | WO 2006/066553 A2 | 6/2006 | | |

OTHER PUBLICATIONS

PCT/US2006/015000—International Search Report and Written Opinion (Sep. 22, 2006).

Inhalation Injry: Pathophysiology and Clinical Care Proceedings of a Symposium Conducted at the Trauma Institute of San Antonion, San Antonio, TX, USA on Mar. 28, 2006.

* cited by examiner

METHOD AND SYSTEM FOR PURGING MOISTURE FROM AN OXYGENATOR

FEDERALLY SPONSORED RESEARCH

This invention was not a result of federally sponsored research.

CROSS-REFERENCES TO RELATED APPLICATIONS

This application claims no priority to any prior application.

BACKGROUND OF THE INVENTION

The present invention relates generally to extracorporeal systems for oxygenating and pumping blood during, for example, cardiac surgery. More specifically, the present invention relates to a method and system for improving gas exchange properties of oxygenators which utilize hollow fiber membranes for removing carbon dioxide and/or adding oxygen to a patient's blood via extracorporeal circulation.

It has been reported that 350,000 Americans die of lung disease each year, most from Acute Respiratory Distress Syndrome (ARDS) and Chronic Obstructive Pulmonary Disease (COPD). The most common treatment is mechanical ventilation, but may further exacerbate respiratory insufficiency and can cause serious side effects, such as barotrauma and volutrauma. It has been further reported that oxygenators are commonly utilized throughout the world in heart-lung machines, which are employed during surgery, and Extra Corporeal Membrane Oxygenation (ECMO) therapy, which is used to treat patients with compromised cardiopulmonary functions. Such oxygenators may be useful in treating COPD and ARDS. However, inefficient mass transfer (gas exchange) of oxygen and carbon dioxide is a common problem in oxygenators used in heart-lung machines and ECMO therapy.

The use of membrane oxygenators to oxygenate blood is well known in the art. Typically, they are disposable components which employ bundles of tiny hollow fibers made from a special polymer material having microscopic pores. The hollow fibers are generally impermeable to blood and permeable to gas. These fiber bundles are contained within a housing which includes an opening or port for receiving venous blood from a patient and an exit port through which the now oxygenated blood exits the oxygenator and is returned to the patient. Blood enters the oxygenator and flows around the outside surfaces of these fiber bundles. At the same time, a gas medium is pumped through the hollow fibers. This gas medium, often referred as a "sweep gas," can be, for example, air, oxygen or an oxygen-rich gas which may also include an additive such as an anesthetic agent. Based on the law of diffusion, the oxygen contained in the sweep gas diffuses through the microscopic pores of the fibers to enrich the venous blood which contacts the outer surface of the hollow fibers. Due to the high concentration of carbon dioxide in the blood arriving from the patient, some carbon dioxide contained in the blood will likewise diffuse through the microscopic pores into the lumens of the fibers and into the sweep gas. The sweep gas is exhausted from the oxygenator after the oxygen enriching process takes place. As a result of this exchange, the oxygen content of the blood will be raised while the carbon dioxide level will be decreased. In some systems, the blood entering the oxygenator can be heated or cooled prior to be returned to the patient.

In the course of oxygenating blood utilizing a conventional oxygenator, water vapor from the patient's blood can permeate the hollow fiber membrane and condense in the membrane's micro-pores. This condensation effectively increases the diffusion length for the gas transfer and reduces gas exchange efficiency of the oxygenator. Concurrently, condensed water can accumulate in the lumens of the fibers and collect in the bottom of the fibers, which can substantially block or at least somewhat diminish the flow of the sweep gas through the fibers. As the number of blocked fibers increases, so too does the pressure drop across the fiber bundle. This accumulation of water in the fibers also affects carbon dioxide exchange because carbon dioxide can build up in the water barrier, thereby decreasing the driving concentration gradient needed for carbon dioxide transfer. When a sufficient number of fibers become blocked, the pressure drop across the bundle reaches that of the surface tension required to push the accumulated moisture from the fiber ends. As a result of this phenomenon, gas exchange gradually decreases until the number of blocked fibers increases to a level where the pressure drop across the oxygenator equals the droplet surface tension and equilibrium is achieved. This accumulation of moisture in the fibers is unwanted and will diminish the gas exchange efficiency of the oxygenator.

"Coughing" of the oxygenator has been described as a method to increase the instantaneous flow across the oxygenator (and associated pressure drop), thereby effecting a purge (removal of the accumulated moisture) similar to a cough in a patient. There are limitations to this method, however. Since the coughing of the oxygenators raises the pressure of the sweep gas compartment (i.e., the lumens of the hollow fiber), the risk of gas embolus forming in the blood and flowing back to the patient is dramatically increased. Accordingly, when the oxygenator is being coughed, the increased pressure of the sweep gas in the hollow fibers should never exceed the pressure in the blood compartment (typically below 200 mmHg). However, since positive pressure is utilized to increase the sweep gas pressure to generate the "cough," it is often difficult, if not impossible, to prevent the sweep gas pressure from becoming higher than the pressure in the blood compartment of the oxygenator.

Accordingly, there is a need for, and what was heretofore unavailable, a method and system for enhancing the gas exchange characteristics of an oxygenator by overcoming the limitations and dangers associated with "coughing" an oxygenator utilizing conventional methods while providing a safe and reliable way to remove accumulated moisture from within the hollow fibers of the oxygenator. The present invention described herein satisfies these and other needs.

SUMMARY OF THE INVENTION

The present invention is directed to a method and system for improving the gas exchange properties of oxygenators which utilize hollow fiber membranes for removing carbon dioxide and/or adding oxygen to a patient's blood via extracorporeal circulation. The present invention improves the gas exchange properties by intermittently removing moisture buildup from the fibers of the oxygenator. The present invention utilizes negative pressure, or a vacuum, to draw the sweep gas into the oxygenator and a moisture purging system which intermittently removes any moisture from the oxygenator. The present invention accomplishes this without the need to increase the pressure of the sweep gas as it enters the fiber bundle of the oxygenator. The moisture purging system of the present invention generates the "cough" that removes moisture from the oxygenator without the need to increase the pressure of the sweep gas entering the oxygenator. Accordingly, there is no increased risk of forming gas emboli in the blood flowing through the oxygenator since the sweep gas is being drawn into, rather than being forced or driven into the oxygenator. This removal of accumulated moisture from the oxygenator can be performed intermittently to insure that there is little possibility of any appreciable moisture accumulating in the fibers for a prolonged period. As a result, the gas exchange rate for the oxygenator should not be affected by moisture accumulation in the oxygenator during usage.

The present invention utilizes a source which will draw the sweep gas into the oxygenator utilizing a vacuum (negative pressure). In one aspect of the present invention, a vacuum pump, for example, could be used to draw the sweep gas into the oxygenator, rather than positively pushing sweep gas into the oxygenator. The vacuum source would be connected to the sweep gas exit port of the oxygenator to draw, rather than drive, the sweep gas through the fiber bundles. As a result of utilizing a vacuum to draw the sweep gas into the oxygenator, rather than using a positive pressure source which pushes or drives the sweep gas into the inlet port of the oxygenator, there is little chance of the sweep gas permeating the fiber membrane into the blood flowing through the oxygenator. Therefore, there is little chance of gas emboli being formed in the blood being returned to the patient during the moisture purging steps described below. In one aspect of the invention, a source for the sweep gas (usually oxygen or air) would be connected to the gas inlet port of the oxygenator. The moisture purging system of the present invention would be connected to the sweep gas outlet of the oxygenator and will create a build up of negative pressure that, when released, will cause a sudden rush of sweep gas though the oxygenator, effectively removing all accumulated moisture.

The moisture purging system of the present invention includes a unit for collecting the moisture being purged from the oxygenator. In one aspect of the present invention, a moisture canister or "water trap" could be used to collect the accumulated fluid. This moisture collecting unit would be connected between the oxygenator and the vacuum source utilizing a conduit, such as conventional flexible tubing, well known in the art.

The moisture purging system further includes a flow control mechanism associated with the moisture collecting unit and the oxygenator. In one aspect of the present invention, the flow control mechanism can be a simple pinch valve which opens and closes the conduit (for example, flexible tubing) connecting the moisture collecting unit to the oxygenator. When the flow control mechanism is placed in the open position, the sweep gas will freely flow through the conduit connecting the oxygenator to the moisture collecting unit as it is being drawn by the vacuum source. When the flow control mechanism is placed in the closed position, fluid communication between the moisture collecting unit and the oxygenator will be temporarily closed. The flow of sweep gas through the oxygenator also will be temporarily stopped. The vacuum source, however, will continue to evacuate any sweep gas contained within the moisture collecting unit, which causes a build up of high negative pressure within the moisture collecting unit itself. After a short duration, the flow control mechanism will be placed back into the open position. When this occurs, sweep gas is again drawn into, and rushes through, the fibers of oxygenator at a high velocity to fill the vacuum created in the moisture collecting unit. The velocity of the sweep gas flow will increase with higher vacuum achieved in the moisture collecting unit. This increase in the velocity of the sweep gas will cause any moisture accumulating in the fibers of the oxygenator to be removed and drawn into the moisture collecting unit with the sweep gas. As the vacuum developed in the moisture collecting unit increases, better moisture purging will take place. As a result, the fibers of the oxygenator can be maintained clear of moisture accumulation during usage.

The flow control mechanism can be connected to a signal source designed to open and close the fluid path between the oxygenator and the moisture collecting unit. The period that the mechanism remains open or closed could be easily programmed into the signal source to activate the moisture purging system. Since it usually takes a bit of time to accumulate moisture in the fibers of the oxygenator, the moisture purging system will usually remain in the open position in which sweep gas is being continually drawn through the oxygenator. The signal source could then provide a signal to the flow control mechanism to assume the closed position, and will dictate the duration that the flow control mechanism will remain in the closed position. After that period is reached, the signal source will move the flow control mechanism back to the open position to purge the moisture from the oxygenator. Again, the duration that the flow control mechanism remains in the open or closed system can be determined and easily adjusted using controls associated with the signal source. The described system is therefore capable of removing moisture from the oxygenator without increasing the pressure within the fibers of the oxygenator and without compromising patient safety.

The moisture purging system of the present invention can be used on a number of different oxygenators which utilize hollow fiber membranes for removing carbon dioxide or adding oxygen to a patient's blood via extracorporeal circulation. The present invention can be utilized with a number of different systems which supply the necessary sweep gas to the oxygenator. Likewise, the moisture purging system of the present invention can be connected with additional instrumentation which can, for example, analyze the oxygen/carbon dioxide content of the sweep gas as it exits the oxygenator. Feedback loop controls could be associated with such equipment and the signal source to adjust the timing of the intervals when the flow control mechanism is placed in either the open or closed position.

Other features and advantages of the invention will become apparent from the following detailed description, taken in conjunction with the accompanying drawings, which illustrate, by way of example, the features of the invention.

DESCRIPTION OF THE PREFERRED EMBODIMENTS

Figure 1:
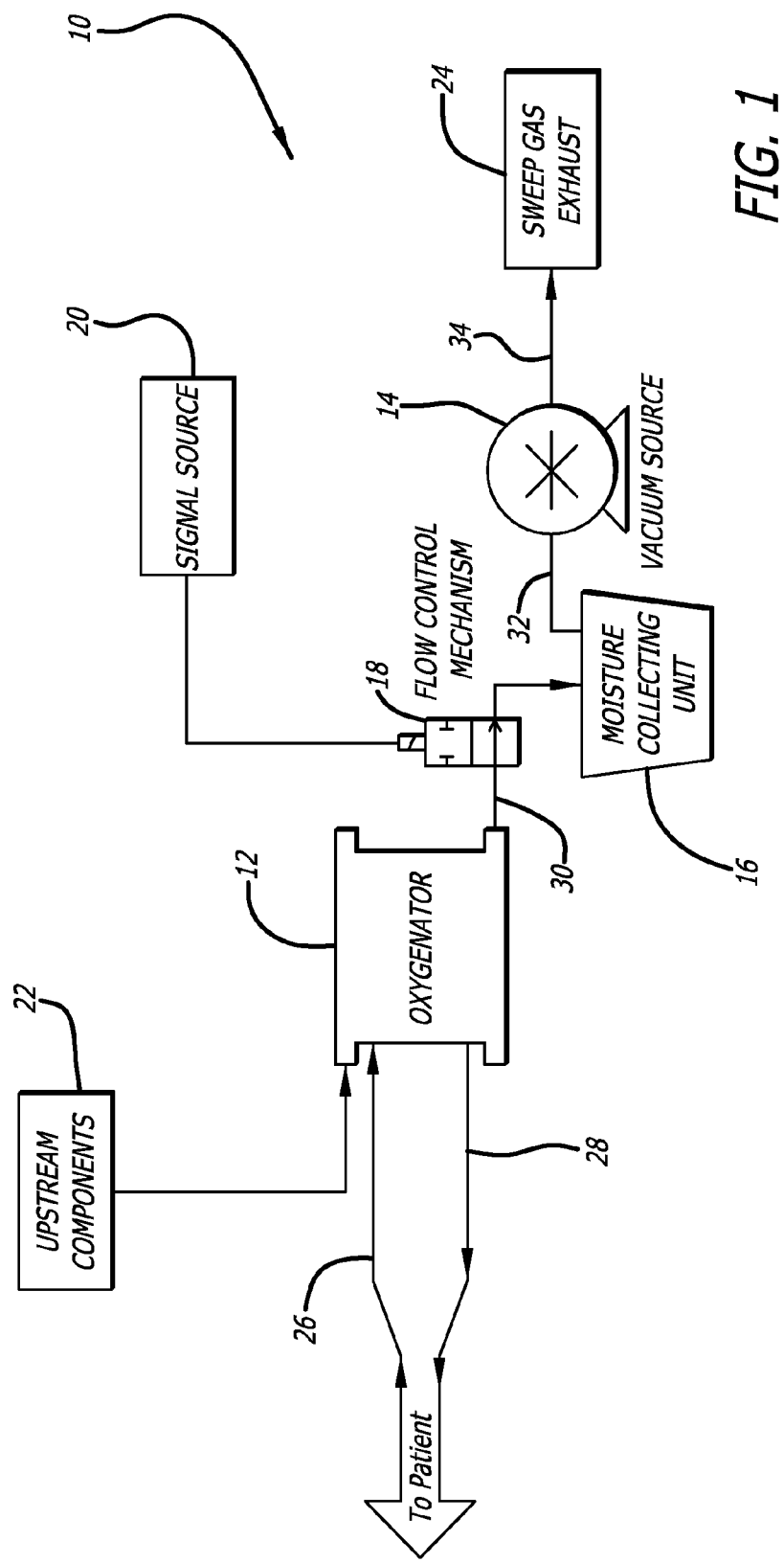
FIG. 1 is a block diagram of the moisture purging system of the present invention.

Referring now to FIG. 1, a block diagram depicting the moisture purging system 10 is shown. The moisture purging system 10 is utilized to remove accumulated moisture from an oxygenator 12 which utilizes hollow fiber membranes for removing carbon dioxide and/or adding oxygen to a patient's blood via extracorporeal circulation. The moisture purging system 10 includes a vacuum source 14, shown in FIG. 1 as a vacuum pump, which is in communication with the sweep gas exit port of the oxygenator. The moisture purging system 10 further includes a moisture collecting unit 16 which, in FIG. 1, is shown as a moisture canister or water trap which is a well known device utilized in medical and other systems for collecting unwanted moisture from a system. Lastly, the moisture purging system 10 includes a flow control mechanism 18 shown as a pinch valve in FIG. 1. It would be appreciated by those skilled in the art that this flow control mechanism can be any one of a number of different mechanisms which basically opens or closes fluid communication between the moisture collecting unit 16 and the oxygenator 12. A signal source 20 is associated with the flow control mechanism 18 to intermittently provide a signal to place the flow control mechanism 18 in either an open position or a closed position. When the flow control mechanism 18 is placed in the open position, the moisture collecting unit 16 and the vacuum source 14 are in communication with the oxygenator to draw the sweep gas through the oxygenator. When the flow control mechanism 18 is placed in the closed position, communication between the moisture collecting unit 16 and the oxygenator is closed, which allows the vacuum source 14 to evacuate any sweep gas contained within the moisture collecting unit 16. This causes a buildup of negative pressure within the moisture collecting unit itself. After a short duration, the flow control mechanism 18 can then be placed back in the open position, which causes the sweep gas to again flow through the fibers of the oxygenator at a much higher velocity to fill the vacuum within the moisture collecting unit. When this occurs, any moisture which may have been accumulating within the fibers of the oxygenator will be drawn in with the sweep gas exiting the oxygenator and will be collected in the moisture collecting unit 16. In this fashion, the oxygenator has been "coughed" to purge moisture from the oxygenator without the need to increase the pressure of the sweep gas within the oxygenator.

As is shown schematically in FIG. 1, the oxygenator 12 is connected to upstream components 22 which provide the sweep gas that will be entering the oxygenator 12. A suitable system to provide sweep gas is disclosed in FIG. 2 and will be described in greater detail below. The sweep gas which exits the oxygenator is ultimately sent downstream as sweep gas exhaust 24. The moisture purging system 10 of the present invention can be connected to additional downstream instrumentation which may include, for example, an oxygen sensor or a carbon dioxide analyzer used to monitor the oxygen and carbon dioxide content in the sweep gas exhaust. A system for analyzing the sweep gas exiting the vacuum source 14 is disclosed in FIG. 2 below and will be described in greater detail below.

The oxygenator 12 includes inlet and outlet ports (schematically depicted in FIGS. 1 and 2) through which venous blood enters and exits the oxygenator 12. Once the venous blood has been oxygenated by the system, the oxygen-enriched blood can then be returned to the patient. FIG. 1 schematically depicts inlet line 26, which provides the venous blood to the oxygenator, and outlet line 28, which provides the oxygen-enriched blood back to the patient. It should be appreciated that a separate delivery system could be utilized to remove and return the oxygen-enriched blood to the patient. Such a system may include safety mechanisms such as flow and bubble detectors and other instrumentation to ensure safety in infusing the oxygen-enriched blood back to the patient.

The oxygenator 12 depicted in FIG. 1 can be any one of a number of different commercially-available oxygenators. These hollow fibers are generally impermeable to blood, and permeable to gas. The fiber bundles are contained within the housing of the oxygenator 12 which, as mentioned above, includes a blood inlet port for receiving the venous blood from the patient. The oxygen-enriched blood then exits the oxygenator 12 and is returned to the patient. The venous blood which enters the oxygenator 12 flows around the outside surfaces of the fiber bundles. At the same time, the sweep gas, which can be, for example, air, oxygen, or an oxygen-rich gas, is pumped into the hollow fibers. Based on the law of diffusion, the oxygen contained in the sweep gas diffuses through the microscopic pores of the fibers to enrich the venous blood which contacts the outer surface of the hollow fibers. Due to the high concentration of carbon dioxide in the blood arriving from the patient, some carbon dioxide contained in the blood will likewise diffuse through the microscopic pores into the lumens of the fibers and into the sweep gas. The sweep gas is exhausted from the oxygenator 12 after the oxygen enriching process takes place. As a result of this exchange, the oxygen content of the blood is increased while the carbon dioxide level will decrease. Suitable oxygenators which can be utilized in accordance with the moisture purging system 10 of the present invention are disclosed in U.S. patent application Ser. No. 11/408,650 and the following references: U.S. Pat. Nos. 5,830,370 (Maloney et al.); 5,900,142 (Maloney et al.); 6,106,776 (Borovetz et al.); 6,217,826 (Reeder et al.); 6,348,175 (Borovetz et al.); 6,723,284 (Reeder et al.) and U.S. Publication No. 2004/0219061 (Reeder et al.), which are incorporated herein in their entirety by reference.

When the moisture purging system 10 is in use, the system 10 will intermittently remove any accumulated moisture in the hollow fibers and the fiber membrane micropores of the oxygenator 12. The system operates when venous blood is supplied to the oxygenator 12 via the inlet line 26 from a patient. The vacuum source 14, shown as a vacuum pump in FIG. 1, will draw sweep gas from the upstream components 22 through the fibers which are located within the housing of the oxygenator 12. As can be seen in FIG. 1, there are a number of conduits or lines which are utilized to communicate with the oxygenator 12. An outlet line 30 connects the moisture collecting unit 16 to the outlet port of the oxygenator 12. Another outlet line 32 is utilized to connect the vacuum source 14 to the moisture collecting unit 16. Lastly, a sweep gas exhaust line 34 directs the sweep gas exiting the oxygenator 12 to additional downstream analyzers or to a simple exhaust port which removes the sweep gas to the room. The flow control mechanism 18, shown as a pinch valve in FIG. 1, is associated with the moisture collecting unit 16 and the oxygenator 12 in order to place the outlet line 30 in either an open position or a closed position. It should be appreciated that a pinch valve is utilized in conjunction with the present embodiment, since the inlet and outlet lines which are typically used in such a medical system are generally made from flexible tubing, which is both disposable and easy to install/remove from the system. The pinch valve is a simple mechanism which basically includes a pinch mechanism which "pinches" or squeezes the flexible tubing to stop the flow of sweep gas through that particular line.

When the pinch valve is placed in an open position, sweep gas can freely flow through outlet line 30 into the moisture collecting unit 16. Since the vacuum source 14 is in fluid communication with both the moisture collecting unit 16 and the oxygenator 12, the negative pressure or vacuum created by the vacuum source 14 will draw the sweep gas through the oxygenator 12, rather than having the sweep gas delivered by a direct pressurized source which drives the sweep gas into the oxygenator.

The vacuum source 14 will maintain a substantially steady flow of the sweep gas through the oxygenator 12 when the pinch valve is in the open position. Generally, the system remains in a normal operating mode in which the pinch valve remains in the open position to allow the blood to be continuously enriched by the oxygenator. When the moisture purging steps are to be performed by the system 10, the signal source 20 will deliver a signal to the pinch valve which will cause the system to enter a "high vacuum mode." The pinch valve moves into its closed position, temporarily preventing the vacuum source 14 from drawing any sweep gas through the oxygenator 12. When the pinch valve is in the closed position, the vacuum source 14 continues to draw a vacuum through outlet line 32, which results in any sweep gas contained in the moisture collecting unit 16 to be drawn out by the vacuum source. As a result, negative pressure or a vacuum will be created in the moisture collecting unit for a brief time. The signal source 20 will then initiate the pinch valve to move to the open position, which opens communication between the moisture collecting unit 16 and the oxygenator 12. When this occurs, the negative pressure now present in the moisture collecting unit 16 will quickly draw the stagnant sweep gas through the oxygenator 12 at a high velocity which causes any moisture accumulated in the fibers to be swept in with the sweep gas into the moisture collecting unit 16. In this fashion, any accumulated moisture in the fibers of the oxygenator 12 will be safely removed without the risk of creating gas emboli in the blood being returned to the patient. This again is achieved since the pressure of the sweep gas which is entering the oxygenator does not have to be increased, as is done in conventional "coughing" procedures. Since the moisture purging system 10 of the present invention does not increase the pressure of the sweep gas entering the oxygenator 12, there is little or no chance of any sweep gas being pushed through the micropores of the fibers into the blood compartment of the oxygenator 12. Rather, by subjecting the now stagnant sweep gas to a sudden high velocity flow caused by the negative pressure in the moisture collecting unit 16, a "cough" is generated which will draw any accumulated moisture with the sweep gas into the moisture collecting unit 16. As a result, a much safer system is utilized to purge any moisture from the oxygenator 12 during use.

It should be appreciated that, while a flow control mechanism 18 is shown attached to the outlet line 30, it is also possible to incorporate such a mechanism directly into the moisture collecting unit 16 as well. Alternatively, the flow control mechanism 18 may be incorporated into the system at the sweep gas inlet to the oxygenator 12. Suitable flow control mechanisms include various types of solenoid valves and well-known mechanisms which can either open or close fluid communication between components.

Figure 2:
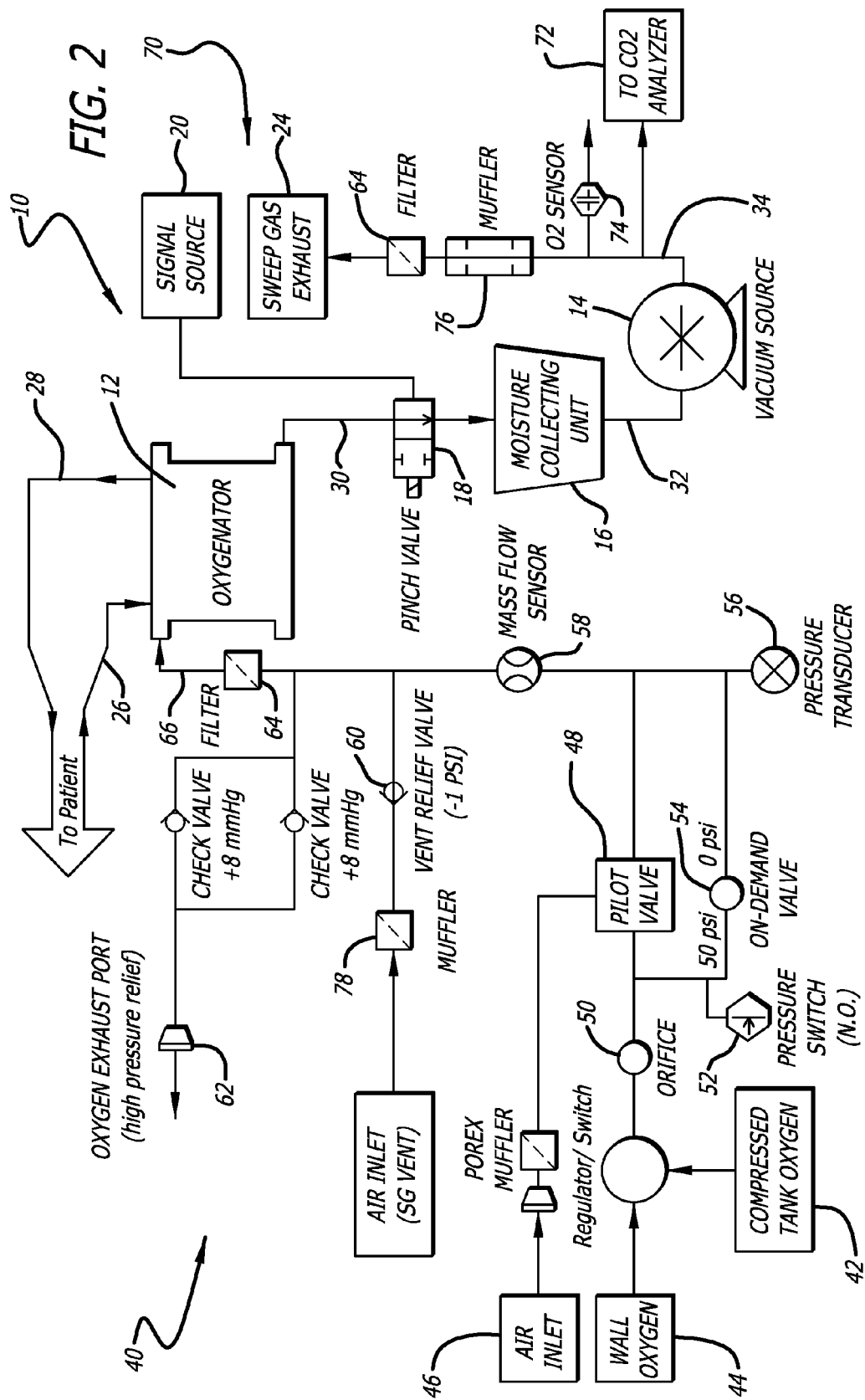
FIG. 2 is a block diagram of a particular system which incorporates the moisture purging system of the present invention.

Referring now to FIG. 2, the moisture purging system 10 of the present invention is shown configured with additional systems which provide the sweep gas to the oxygenator 12 and analyze the downstream sweep gas being discharged from the vacuum source 14. The particular system shown in FIG. 2 constitutes the upstream components 22 which are schematically depicted in FIG. 1. The downstream instrumentation attached to the moisture purging system 10 in FIG. 2 is utilized to analyze the sweep gas being exhausted from the vacuum source. The moisture purging system 10 disclosed in FIG. 2 consists of the same basic components disclosed in FIG. 1 and described above.

A suitable system 40 for supplying the sweep gas to the oxygenator 12 is disclosed in FIG. 2 and can be run either from an oxygen or air supply. In a hospital situation, the sweep gas is generally provided by an oxygen source which is easily accessible in a hospital room. For example, oxygen in a hospital or patient treatment area can be supplied from a compressed oxygen tank 42 or a wall valve 44 which is connected to a main dedicated oxygen which supplies oxygen to all patient rooms in the hospital. The sweep gas supply system 40 also could utilize an air inlet 46 which supplies room air, rather than pure oxygen, as the sweep gas.

As can be seen in FIG. 2, there are a number of valves and regulators connected to either the air supply 46 or the compressed oxygen tank 42 or wall valve 44. In the oxygen based system of FIG. 2, pilot valve 48 is utilized to change the sweep gas to air from the back up air inlet 46, if for some reason, the oxygen supply is not available or becomes diminished. This could occur, for example, should the oxygen tank run out of oxygen. Oxygen flow enters the system 40 generally at about 50 psi and is limited by the orifice 50 to a value just above the maximum sweep gas flow setting, as a safety measure. The system controller detects the presence of oxygen using a pressure switch 52. If the system 40 is running on oxygen, an on-demand valve 54 reduces the pressure from 50 psi to atmospheric pressure (0 psi). A pressure sensor transducer 56 is used to measure the sweep gas pressure while a mass flow sensor 58 measures the sweep gas flow through the system. A safety feature is provided which prevents the sweep gas system 40 from experiencing too much vacuum once the flow control mechanism 18 is released and the system is once again placed in the open position or "high vacuum" mode. This is accomplished by the vent relief valve 60. An oxygen exhaust port 62 is utilized as a redundant safety mechanism to prevent overpressurization if the on-demand valve 54 were to fail. A filter 64 is utilized to filter any unwanted particles which may be entrained in the sweep gas entering the oxygenator 12.

The sweep gas line 66 is attached to the disposable oxygenator 12. The outlet line 30 is connected to the moisture purging system 10 with the outlet line 30 being fed through the pinch mechanism associated with the pinch valve. The vacuum source 14, usually a vacuum pump, is used to generate the sweep gas flow under system control. It should be noted that the controls for the pump are not depicted in FIG. 2. Suitable system controls could be utilized to obtain the necessary vacuum to be developed to draw the sweep gas through the oxygenator 12.

The sweep gas which exits the vacuum source 14 can be analyzed to determine, for example, the gas efficiency of the oxygenator 12. In FIG. 2, this downstream system 70 is shown as a $CO_2$ analyzer 72 and an oxygen sensor 74 connected to the sweep gas line 34. These particular instruments can then determine the oxygen content and carbon dioxide content of the sweep gas leaving the oxygenator 12, to determine the gas efficiency of the system. Mufflers 76 and 78 may be added to the system for noise reduction. A filter could also be utilized in the sweep gas delivery system 40 shown in FIG. 2. Any remaining sweep gas can be exhausted through a line which will discharge the exhaust into the patient's room. It should be appreciated that the moisture purging system 10 of the present invention could also be connected with other sensors and analyzers in order to calculate the efficiency of the oxygenator 12.

Suitable components for the moisture purging system include a conventional pinch valve sold under the name SV23 Pinch Valve by Valcor Engineering Corporation. Other suitable devices which can be used for the flow control mechanism include any type of valve, whether controlled by pneumatic, manual, or electrical methods, solenoid valves, stopcocks, or any manual method. A suitable moisture collecting unit is a water trap or moisture container sold by Allied Healthcare Products, Inc. under the name 1500 mL Disposable Collection Canister. Still other commercially available water traps could be utilized. A suitable vacuum source includes a vacuum pump sold by KNF Neuberger, Inc. Suitable controls for regulating the vacuum pump are well known. The signal source 20 of the moisture purging system includes anyone of a number of commercially available units which are capable of providing a suitable signal to the flow control mechanism. The signal source could include a user interface for programming and altering the various time settings needed to activate the moisture purging system.

The time intervals between successive moisture purges of the system 10 can vary depending on a number of variables, including the particular model of oxygenator being attached to the system. Additionally, the time period for which the system is maintained in the closed position, during which a high vacuum is generated, will vary. Generally, the system will be maintained in the open position or the normal operational mode, for the majority of the time that the oxygenator is in service. A suitable time interval between successive moisture purges is 15 minutes. A suitable time period for the flow control mechanism to remain in the closed position is 30 seconds. Again, these time periods can vary depending on a number of variables. The time periods can be adjusted accordingly.

While particular forms of the invention have been illustrated and described, it will also be apparent to those skilled in the art that various modifications can be made without departing from the inventive concept. References to use of the invention with a particular oxygenator are by way of example only, and the described embodiments are to be considered in all respects only as illustrative and not restrictive. The present invention may be embodied in other specific forms without departing from its spirit or essential characteristics. Accordingly, it is not intended that the invention be limited except by the appended claims

We claim:

1. A system for removing moisture from an oxygenator which utilizes a sweep gas that flows through hollow fibers forming a portion of the oxygenator to remove carbon dioxide or add oxygen to a patient's blood entering the oxygenator, comprising:
   the oxygenator capable of having a moisture build up within the hollow fibers;
   a vacuum source for drawing sweep gas into the oxygenator;
   a moisture collection unit for storing moisture removed from the oxygenator, the moisture collecting unit being in communication with the oxygenator and the vacuum source; and
   a flow control mechanism having an open position which allows sweep gas exiting the oxygenator to flow to the moisture collecting unit and a closed position which stops the flow of sweep gas from the oxygenator to the moisture collecting unit, wherein the vacuum source draws sweep gas through the oxygenator and moisture collecting unit when the flow control mechanism is in the open position and the vacuum source creates a buildup of negative pressure in the moisture collecting unit when the flow control mechanism is in the closed position; and
   whereby the moisture is removed from the hollow fibers intermittently by an impulse of sweep gas at a higher flow rate created by a release of the negative pressure caused by opening the flow control mechanism after the flow control mechanism had been closed for a period of time, and whereby removing the moisture from the hollow fibers is accomplished without raising a positive pressure of the sweep gas.

2. The system of claim 1, further including a signal source in communication with the flow control mechanism for providing a signal to the flow control mechanism to move the flow control mechanism between the open position and the closed position.

3. The system of claim 1, wherein a flexible tubing connects the oxygenator to the moisture collecting unit and the flow control mechanism is a pinch valve having a pinch mechanism which pinches a portion of the flexible tubing to place the flow control mechanism in the closed position.

4. The system of claim 1, wherein the vacuum source is a vacuum pump which is in communication with the oxygenator.

5. The system of claim 1, further including a system for providing sweep gas to the oxygenator which includes a regulator which prevents the pressure of the sweep gas entering the oxygenator from exceeding a pre-determined limit.

6. The system of claim 2, wherein the signal source automatically provides an intermittent signal to the flow control mechanism to move the flow control mechanism between the open and closed positions at specified time intervals for pre-determined time periods.

7. The system of claim 1, further including a system incorporated into the sweep gas system which limits the amount of negative pressure which can be experienced by the components and equipment within the sweep gas system during the moisture purge immediately following the flow control mechanism's transition from a closed to an opened position.

8. A system for removing moisture from an oxygenator which utilizes a sweep gas that flows through hollow fibers forming a portion of the oxygenator to remove carbon dioxide and/or add oxygen to a patient's blood entering the oxygenator, comprising:
   the oxygenator capable of having a moisture build up within the hollow fibers;
   a vacuum source for drawing sweep gas into the oxygenator;
   a moisture collection unit for storing moisture removed from the oxygenator, the moisture collecting unit being in communication with the oxygenator and the vacuum source, wherein the system operates under a normal vacuum condition in which the vacuum source draws sweep gas through the oxygenator at a substantially constant flow rate and a "high vacuum" condition in which the sweep gas is being drawn through the oxygenator as an impulse at a higher flow rate than when the system is in the normal vacuum position, the system allowing any moisture accumulating in the hollow fibers of the oxygenator to be swept with the sweep gas into the moisture collecting unit when the system is intermittingly in the high vacuum condition without increasing a positive pressure of the sweep gas.

9. The system of claim 8, further including a mechanism for intermittently changing the system between the normal vacuum condition and the high vacuum condition during usage.

10. The system of claim 8, wherein a vacuum developed in the moisture collecting unit helps to draw the sweep gas through the oxygenator when the system is in the high vacuum condition.

11. The system of claim 10, wherein the drawing of sweep gas through the oxygenator by the vacuum source is temporarily stopped to allow the vacuum source to achieve the vacuum in the moisture collecting unit just before the system enters the high vacuum condition.

12. The system of claim 8, wherein the moisture collecting unit is connected between the oxygenator and the vacuum source.

13. A method for removing moisture from an oxygenator which utilizes a sweep gas that flows through hollow fibers forming a portion of the oxygenator to remove carbon dioxide and/or add oxygen to a patient's blood entering the oxygenator, comprising:

connecting the oxygenator capable of having a moisture build up in the hollow fibers to a vacuum source and a moisture collecting unit;

drawing sweep gas at a substantially constant flow rate through the oxygenator and the moisture collecting unit utilizing the vacuum source;

temporarily stopping the flow of sweep gas being drawn into the oxygenator by the vacuum source on an intermittent basis;

creating a vacuum in the moisture collecting unit while the flow of sweep gas through the oxygenator has been temporarily stopped; and increasing the flow rate of the sweep gas creating an impulse of the sweep gas through the oxygenator above the constant flow rate by applying the vacuum created in the moisture collecting unit with the vacuum supplied by the vacuum source; whereby moisture is removed from the hollow fibers without increasing a positive pressure of the sweep gas.

14. The method of claim 13 further including:

collecting any moisture accumulating in the fibers of the oxygenator in the moisture collecting unit when the flow of the sweep gas is increased.

15. The method of claim 13 further including:

providing a source for the sweep gas which maintains the pressure of the sweep gas entering the oxygenator at or below a pre-determined level.

16. A method for removing moisture from an oxygenator which utilizes a sweep gas that flows through hollow fibers forming a portion of the oxygenator to remove carbon dioxide and/or add oxygen to a patient's blood entering the oxygenator, comprising:

providing a system including a vacuum source, a moisture collection unit for storing moisture removed from the oxygenator, the moisture collecting unit being in fluid communication with the oxygenator and the vacuum source and a flow control mechanism having an open position which allows fluid communication between the moisture collecting unit and the oxygenator and a closed position which stops fluid communication between the moisture collecting unit and the oxygenator;

attaching the moisture collecting unit and the vacuum source to the oxygenator;

providing blood flaw into the oxygenator;

placing the control flow mechanism in the open position;

drawing sweep gas through the oxygenator and the moisture collecting unit utilizing the vacuum source;

placing the flow control mechanism in the closed position;

removing any sweep gas contained in the moisture collecting unit and creating a negative pressure vacuum in the moisture collecting unit;

placing the flow control mechanism in the open position to increase the flow rate and to create an impulse of the sweep gas being drawn into the oxygenator; said impulse removing moisture that has accumulated in the hollow fibers and collecting any moisture which has accumulated in the hollow fibers of oxygenator which becomes entrained in the sweep gas when the flow rate is increased in the moisture collecting unit; whereby placing the flow control mechanism in the closed position is done on an intermittent and temporary basis and whereby moisture is suddenly removed from the hollow fibers without increasing a positive pressure of the sweep gas.

17. The method of claim 16 further including:

a signal source associated with the system which intermittently moves the flow control mechanism between the open and closed positions.

18. The method of claim 17, wherein a flexible tube connects the oxygenator to the moisture collecting unit and the flow control mechanism is a pinch valve which includes a pinching mechanism capable of pinching the tubing to place the pinch valve in the closed position.

19. The method of claim 17 further including:

a source for the sweep gas which regulates the pressure of the sweep gas entering the oxygenator.

20. A method for removing moisture from an oxygenator which utilizes a sweep gas that flows through hollow fibers forming a portion of the oxygenator to remove carbon dioxide or add oxygen to a patient's blood entering the oxygenator, comprising:

connecting the oxygenator to a vacuum source and a moisture collecting unit;

drawing sweep gas at a substantially constant flow rate through the oxygenator and the moisture collecting unit utilizing the vacuum source;

temporarily increasing the flow and creating an impulse of sweep gas being drawn into the oxygenator by the vacuum source to a rate that achieves a pressure drop across the device capable of clearing the hollow fibers blocked with moisture on an intermittent basis without increasing a positive pressure of the sweep gas; and returning the flow rate to a substantially constant flow rate following the moisture purge.

* * * * *